| (12) | United States Patent | (10) Patent No.: | US 8,940,146 B2 |
|---|---|---|---|
| | Trones et al. | (45) Date of Patent: | Jan. 27, 2015 |

(54) DEVICE FOR ELECTRO MEMBRANE EXTRACTION

(75) Inventors: Roger Trones, Krakstad (NO); Trond Lovli, Askim (NO)

(73) Assignee: Greibrokk & Trones Septech AS, Kolbotn (NO)

( * ) Notice: Subject to any disclaimer, the term of this patent is extended or adjusted under 35 U.S.C. 154(b) by 327 days.

(21) Appl. No.: 13/312,377

(22) Filed: Dec. 6, 2011

(65) Prior Publication Data

US 2012/0186979 A1     Jul. 26, 2012

Related U.S. Application Data

(60) Provisional application No. 61/419,889, filed on Dec. 6, 2010.

(51) Int. Cl.
  *G01N 1/40*   (2006.01)
  *B01D 61/38*  (2006.01)

(52) U.S. Cl.
  CPC ...... *G01N 1/4005* (2013.01); *G01N 2001/4011* (2013.01); *G01N 2001/4016* (2013.01); *B01D 61/38* (2013.01)
  USPC ........... 204/544; 204/541; 204/601; 204/644; 204/548

(58) Field of Classification Search
  CPC .............. G01N 1/4005; G01N 2001/4011; G01N 2001/4016; B01D 61/38
  USPC ......................... 204/544, 541, 548, 601, 644
  See application file for complete search history.

(56) References Cited

U.S. PATENT DOCUMENTS 5,273,525 A * 12/1993 Hofmann .................. 604/21
2010/0072066 A1 * 3/2010 Pedersen-Bjergaard et al. ..................... 204/540

FOREIGN PATENT DOCUMENTS

| WO | 00/33050 A1 | 6/2000 |
| WO | 2007/004892 A1 | 1/2007 |

OTHER PUBLICATIONS

European Search Report issued in counterpart European Patent Application No. EP 11191853 dated Apr. 8, 2014 (3 pages).
I. Kjelsen et al.; "Low-Voltage Electromembrane Extraction of Basic Drugs From Biological Samples"; Journal of Chromatography A, 1180, pp. 1-9; 2008 (9 pages).

* cited by examiner

*Primary Examiner* — Keith Hendricks
*Assistant Examiner* — Salil Jain
(74) *Attorney, Agent, or Firm* — Osha Liang LLP (57) ABSTRACT

A device for electro membrane extraction has a syringe holder adapted to hold a syringe having an acceptor solution, and a sample vial holder adapted to hold a sample vial having a vial cap, where the vial cap includes an inside funnel to be equipped with a prewetted hollow fiber membrane having a tube like shape sealed at the end opposite the funnel and forming a lumen, and steering guides for at least two electrodes, a first electrode to be immersed in a donor solution placed in the sample vial, a second electrode to be immersed, through the funnel in the vial cap, into the lumen of the hollow fiber membrane, and a positioning device for sliding the first electrode in and out of the donor solution in the sample vial and for sliding the second electrode in and out of the lumen of the hollow fiber membrane.

9 Claims, 6 Drawing Sheets

DEVICE FOR ELECTRO MEMBRANE EXTRACTION

FIELD OF THE INVENTION

The present invention relates to a new device for isolation, purification, concentration and/or enrichment of an organic or biochemical compound through electro membrane extraction, earlier termed as electro kinetic migration, as well as an improved process for the use of said device.

BACKGROUND OF THE INVENTION

The analytical organic chemistry and biochemistry is faced with the problem of providing a compound to be detected in a solution that is suitable for detection by one or more of the commonly known methods. One problem may be that the compound appears in a complex mixture from which it must be isolated. Another problem may be that the compound may be present in a very low concentration. A further problem may be that the sample including the compound to be detected is very small.

There has therefore been developed many different methods for separating, isolating, concentrating and purifying organic compounds. These are well-known procedures for a person skilled in the art and examples are 2-phase extraction (e.g. aqueous phase-organic phase), and 3 phase extractions (e.g. aqueous phase-organic phase-aqueous phase).

From WO0033050 there are known methods and apparatus for 2-phase liquid and 3-phase liquid micro extraction for obtaining a high enrichment of an analyte in the acceptor solution. However, the process of micro extraction is based on diffusion of the analyte and this is a slow process. Further, the achievable end concentration of the analyte depends on the equilibrium conditions for each of two 2-phase-systems, and may result in very low yields, if any.

Even though the above-mentioned processes have been automated, they are still time consuming and generate a lot of organic solvent waste.

In order to improve the required time for this type of isolation procedures, a further development has constituted of the introduction of electro membrane extraction.

It is well known that ionized chemical and biochemical substances migrate in solution under the application of an electrical potential difference. This type of transport, which is called electro kinetic migration, is the basis for electrophoresis, and is also widely used for isolation purposes both in industrial applications (purification) and in the field of analytical chemistry (sample preparation).

Frequently, isolation based on electro membrane extraction is carried out in an aqueous one-phase system. One important example of this is electro dialysis, where ionized chemical substances are transferred from an aqueous donor compartment, through the pores of an ion-exchange membrane filled with the same aqueous medium, and into an aqueous acceptor compartment. In electro dialysis, migration selectivity, which is responsible for isolation, is gained by the presence of small pores in the polymeric membrane, preventing larger molecules from entering the acceptor compartment. Electro dialysis is an important industrial purification and desalting process, and has also been reported as a sample preparation technique in analytical chemistry. However, the ion-exchange membranes used in electro dialysis processes are easily polluted and must be replaced frequently.

Electro membrane extraction has also been accomplished, in a 5-compartment dialyzer with two platinum electrodes and a rigid anion-exchange membrane, where it was shown that nickel ions could cross two two-phase boundaries. The work reported has focused on fundamental migration theory of nickel ions in a system with relatively thick membranes of organic solvent ($\approx 0.2$ cm).

US2010072066A1 disclose a method for isolation, purification, concentration and/or enrichment of an organic or biochemical compound through electro kinetic migration i.e. electro membrane extraction.

There is a need for new, improved processes and devices for isolation, purification, enrichment and/or concentration of an organic compound from a solution, wherein the organic compound is present in a complex mixture or in low concentrations. Further there is a need for new processes giving a high yield of the required organic compound. There is further a need for new processes, which makes it possible to achieve a high purity, and last but not least there is a need for new processes by which the isolation or purification step proceeds significantly faster. Also, there is a need for new processes wherein the environmental issue of large amount of waste organic solvents is resolved.

Figure 1:
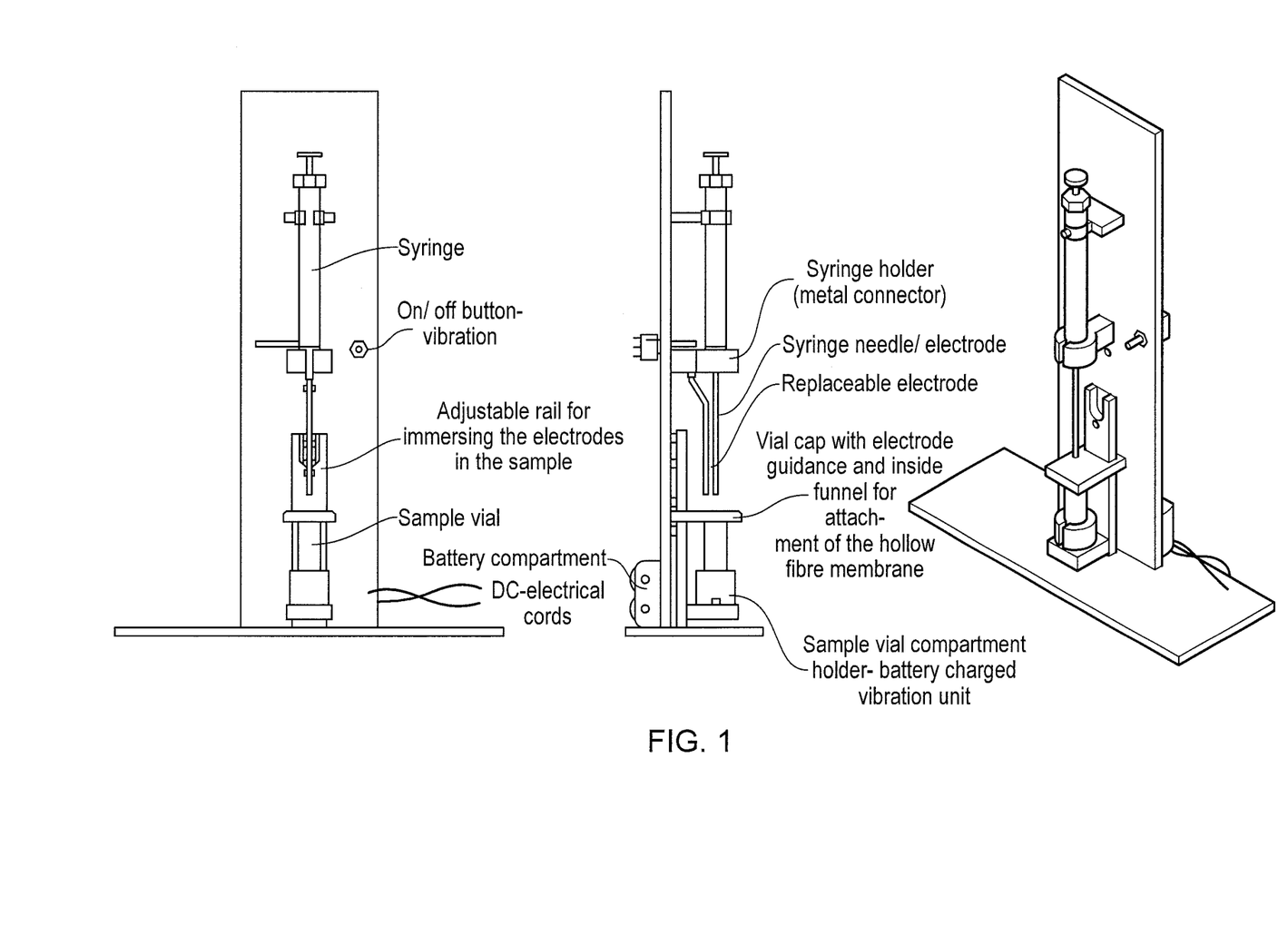
FIG. 1: Illustrates a first embodiment of an electro membrane extraction (EME) device.
Figure 2:
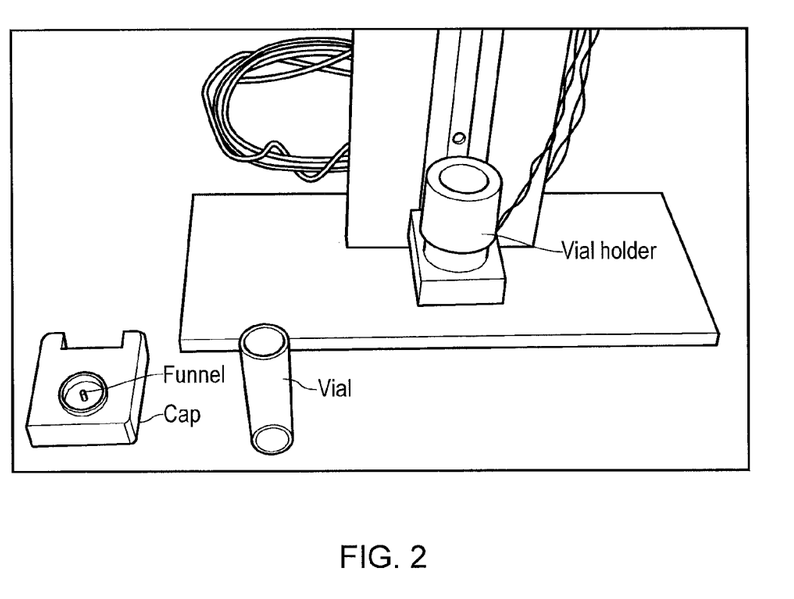
FIG. 2: Shows the vial cap (with inside funnel for attachment of the HFM), the sample vial (donor phase) and the sample vial compartment holder.
Figure 3:
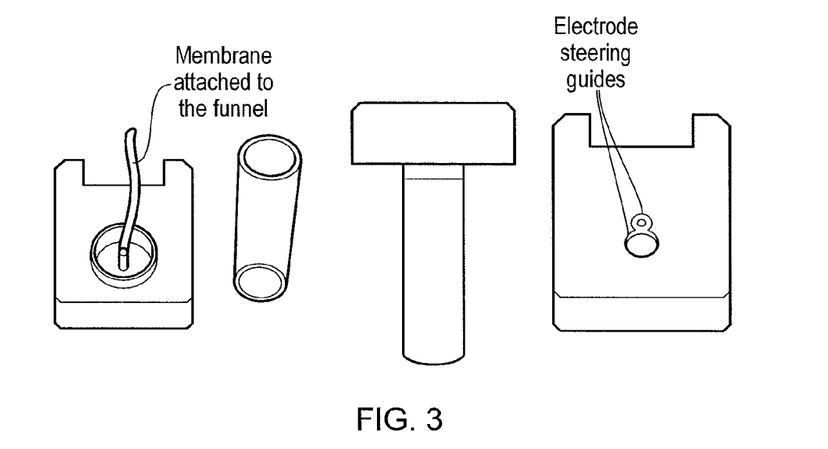
FIG. 3: Shows the vial cap with the attached HFM, the sample vial (donor phase), the vial cap with the inside HFM attached to the sample vial and a top view of the vial cap showing the two electrode guides.
Figure 4:
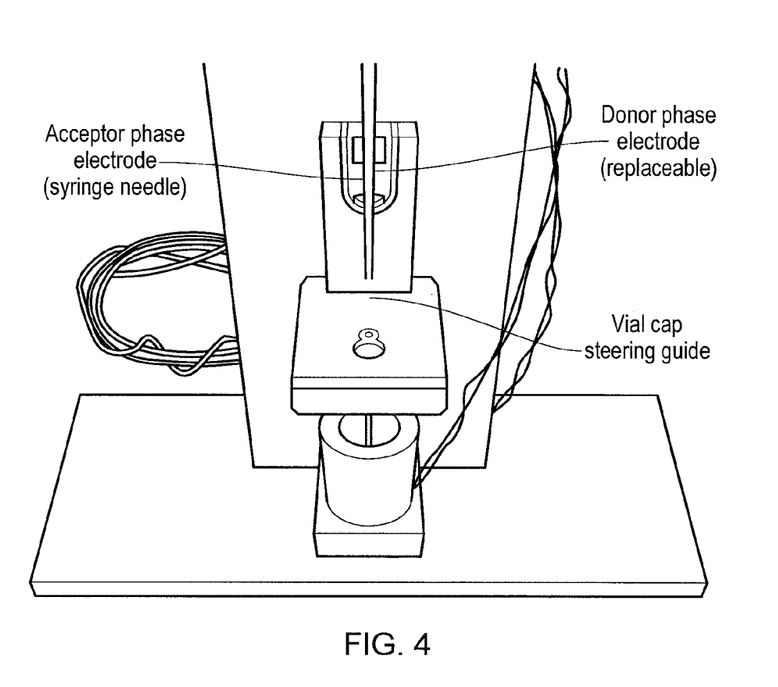
FIG. 4: Shows the filled sample vial with the attached vial cap placed in the sample vial compartment holder. The filled micro syringe is placed in the syringe holder. When the vial compartment holder is pushed upwards, following the vial cap steering guide until it locks into position, the two electrodes will be guided into correct positions by the vial cap electrode guides. The first electrode is immersed in the sample (donor phase) The HFM is filled with acceptor solution from the micro syringe, immersing the last electrode (syringe needle) in the acceptor phase. The device is ready for operation by switching on the vibration unit and connecting the electrical wires to a suitable power source.

A remaining problem to be solved with the process described in US2010/0072066 is the handling and use of the device as described in said application. The device as depicted in FIG. 1 in US2010/0072066 is a first generation device and as such has a potential for improvements. A first embodiment of the present invention as depicted herein (FIGS. 1-4) solve these problems and simplify and improve the whole process of electro membrane extraction, resulting in improved and more reliable results. A second embodiment of the present invention as depicted herein (FIGS. 5-10) is a compacted version of the first embodiment.

SUMMARY OF THE INVENTION

These problems are solved by the present invention through processes and devices according to this invention as defined in the attached claims.

Thus, according to the present invention there is provided a device for electro membrane extraction (EME), comprising a syringe holder adapted to hold a syringe comprising an acceptor solution; a sample vial holder adapted to hold a sample vial comprising a vial cap, where the vial cap includes an inside funnel equipped with a prewetted hollow fiber membrane having a tube like shape sealed at the end opposite the funnel; the vial cap further comprises steering guides for at least two electrodes; a first electrode to be immersed in a donor solution placed in the sample vial; a second electrode to be immersed, through the funnel in the vial cap, into the lumen of the hollow fiber membrane; optionally a vibration/agitation unit; and positioning means for sliding the first electrode in and out of the sample vial (donor solution) and sliding the second electrode in and out of the lumen of the hollow fiber membrane.

In one embodiment of the present invention the syringe needle is used as the second electrode (acceptor phase).

The invention further provides for a process for electro membrane extraction (EME) of an organic compound in a 3-phase system, comprising the steps of
  providing a sample solution comprising at least one organic compound to be extracted in a sample vial,
  attaching a hollow fiber membrane (HFM) to a funnel arranged on the inside of a vial cap,
  dipping the HFM in an organic solvent, thereby forming an artificial liquid membrane;
  placing the vial cap on top of the sample vial, immersing the HFM into the sample solution;

placing a needle of a micro syringe within the inner lumen of the HFM, where the micro syringe comprises an acceptor solution;

placing a sample electrode in the sample solution;

injecting the acceptor solution into the inner lumen of the HFM;

applying power over the sample electrode and the needle to promote the migration of said organic compound from the sample solution through the liquid membrane to the acceptor solution.

In one embodiment the process according to the invention further comprises switching off the power supply and retracting the acceptor solution into the micro syringe.

In one aspect, the process may further comprise agitating the sample by vibration.

In another embodiment of the process according to the invention, the needle is placed within the lumen of the HFM and the electrode is placed within the sample solution in one step.

A further step of the process may include transferring the acceptor solution to a micro insert for further analysis in a dedicated analytical instrument.

The invention can be used in a process for concentration and/or enrichment of at least one organic compound, comprising the steps of providing a first hydrophilic donor solution comprising at least one organic compound to be transferred from said donor solution to an acceptor solution;

the pH of said donor solution being at a level where said organic compound is either positively or negatively ionized, if necessary, by adjusting the pH;

providing a second hydrophilic acceptor solution;

the pH of said acceptor solution being at a level wherein said compound, to be transferred from the donor solution to the acceptor solution, is ionized, if necessary, by adjusting the pH;

providing a liquid membrane whose thickness is in the range of 0.01-1000 μm, comprising an immobilized organic solvent, which is substantially immiscible with water, through which a current and said at least one ionized organic compound can traverse; and placing said membrane in fluid contact with said donor solution and said acceptor solution, so that it separates said donor solution and said acceptor solution;

providing a first electrode to be placed in fluid contact with the donor solution and a second electrode to be placed in fluid contact with the acceptor solution;

applying a voltage over said electrodes to promote the migration of said organic compound from the donor solution through the liquid membrane to the acceptor solution.

The invention can further be utilized in a process for preparing a sample for analysis (isolation), comprising the steps of providing a first hydrophilic donor solution comprising at least one organic compound to be transferred from said donor solution to an acceptor solution;

the pH of said donor solution being at a level where said organic compound is either positively or negatively ionized, if necessary, by adjusting the pH;

providing a second hydrophilic acceptor solution; the pH of said second hydrophilic acceptor solution being at a level wherein said compound to be transferred from the donor solution to the acceptor solution, is ionized, if necessary by adjusting the pH;

providing a liquid membrane whose thickness is in the range of 0.01-1000 μm comprising an immobilized organic solvent, which is substantially immiscible with water, through which a current and said at least one ionized organic compound can traverse; and placing said membrane in fluid contact with said donor solution and said acceptor solution, so that it separates said donor solution and said acceptor solution;

providing a first electrode to be placed in fluid contact with the donor solution and a second electrode to be placed in fluid contact with the acceptor solution;

applying a voltage over said electrodes to promote the migration of said organic compound from the donor solution through the liquid membrane to the acceptor solution;

the pH of said acceptor solution being at a level where said compound to be transferred is ionized, if necessary, by adjusting the pH of the acceptor solution to transfer said organic compound from an ionized to a non-ionized state and/or transferring the organic compound into an organic solvent, and detecting said organic compound by a suitable detector system and/or checking for biological activity in a biological test system.

The invention can further be utilized in a process for purification of a sample, comprising the steps of providing a first hydrophilic donor solution comprising at least one organic compound to be transferred from said donor solution to an acceptor solution; the pH of said donor solution being at a level where said organic compound is either positively or negatively ionized, if necessary, by adjusting the pH;

providing a second hydrophilic acceptor solution;

the pH of said acceptor solution being at a level wherein said compound to be transferred from the donor solution to the acceptor solution is ionized, if necessary, by adjusting the pH;

providing a liquid membrane whose thickness is in the range of 0.011000 μm, comprising an immobilized organic solvent, which is substantially immiscible with water, through which a current and said at least one ionized organic compound can traverse; and placing said membrane in fluid contact with said donor solution and said acceptor solution, so that it separates said donor solution and said acceptor solution;

providing a first electrode to be placed in fluid contact with the donor solution and a second electrode to be placed in fluid contact with the acceptor solution;

applying a voltage over said electrodes to promote the migration of said organic compound from the donor solution through the liquid membrane to the acceptor solution; optionally isolating said at least one organic compound through removal or replacement of the solvent, if necessary, after adjusting the pH of the solution.

DETAILED DESCRIPTION OF THE INVENTION

Electra Membrane Extraction (EME)

The equipment used for electro membrane extraction (EME) is illustrated in FIG. 1-10. The DC power supply used was e.g. a model XFR 300-9 (Xantrex, Burnaby, BC, Canada) with a programmable voltage in the range 0 to 300 V, providing currents in the range 0 to 9 A. A simple steel wire and a syringe needle with a diameter of approx. 0.5 mm were used as electrodes in the sample (donor phase) and acceptor solution, and were connected to the power supply. An approx. 800 µL vial was filled with sample and equipped with a vial cap wherein a pretreated hollow fiber membrane was preinstalled. The glass had a height of approx. 31 mm and an internal diameter of approx. 10 mm. The porous hollow fiber used for immobilization of the artificial liquid membrane and for housing the acceptor solution was a PP Q3/2 polypropylene hollow fiber (Membrana, Wuppertal, Germany) with an internal diameter of 1.2 mm, a wall thickness of 200 µm, and a pore size 0.2 µm. The sample was "agitated" by a vibration unit included in the first embodiment and an external (separate) vibration (e.g. Vibramax 100, Heidolph) unit in the second embodiment. In one aspect the device is configured for use in connection with separate vibration unit which secures thorough mixing of the solutions contained therein.

Figure 9:
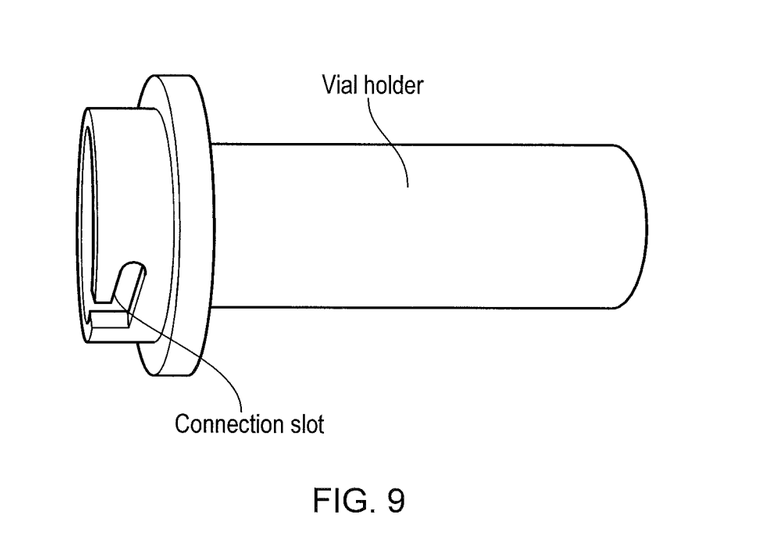
FIG. 9: Shows the connection slot on the vial holder for attaching the vial holder to the main compartment and thereby keeping the vial with the attached vial cap in the main compartment.
Figure 10:
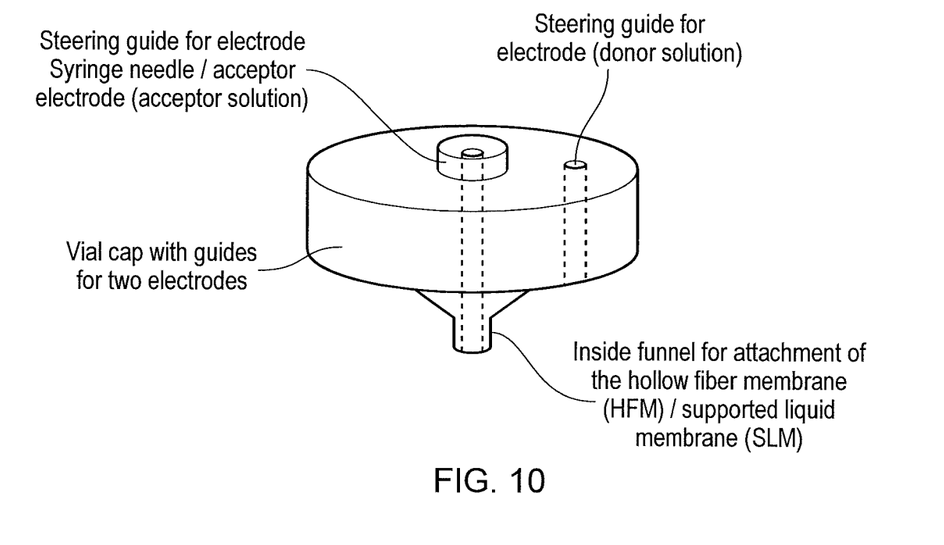
FIG. 10: Illustrates a perspective view of the vial cap including steering guides for two electrodes.

EME was performed according to the following procedure; 300 µl acidified sample (donor phase) solution was filled into a vial. An approx. 3.1 cm piece of a closed tip polypropylene hollow fiber membrane (HFM), was by its open end attached to the inside funnel of the vial cap, dipped for 5 s in a organic solvent, serving as the artificial liquid membrane (typically 2-nitrophenyl octyl ether, nitrobenzene, 1-iso-propyl nitrobenzene, octanol or heptanal). Excess of solvent was carefully removed with e.g. a medical wipe. The vial cap with the attached and pretreated hollow fiber membrane was then placed on top of the sample vial, immersing the HFM into the sample (donor) solution. The sample vial was placed in the sample vial holder compartment. In the second embodiment, where the holder as illustrated in FIG. 9 comprises at least one connection slot at the end to be connected to the main compartment and the main compartment comprises a protruding element adapted to fit into the slot to establish a releasable connection. A preloaded micro syringe was placed in the syringe holder (both embodiments). In the first embodiment the sample vial compartment was pushed upwards, guided by the adjustable rail, to immerse the sample electrode (donor phase). In the second embodiment the placing of the syringe in the syringe holder after the vial has been placed in the main compartment by connecting the vial holder to the main compartment part of the device results in the needle of the syringe being arranged in the lumen of the HFM. In both embodiments approx. 30 µL of acceptor solution was filled from the syringe into the lumen of the HFM, immersing the acceptor phase electrode (syringe needle). Both electrodes were steered into their correct positions by the electrode guidance in the vial cap. Finally, the vibration unit was activated and, voltage (typically 0-300 V) was applied for e.g. 5 minutes. After electro membrane extraction, the acceptor solution was collected with the micro syringe, and subsequently transferred to a micro insert for further analysis in a dedicated analytical instrument.

Theoretical Understanding

Without being bounded by theory, the inventors consider the following to be the theoretical basis of the present inventive concept: In order to enable EME, the whole system comprising the sample solution, the artificial liquid membrane, and the acceptor solution should serve as an electrical circuit. The major electrical resistance of the system was focused in the artificial liquid membrane, and the solvent used here was critical in order to ensure penetration of the electrical energy. Thus, a solvent with a certain polarity or water content should be used to give sufficient electrical conductance, and to ensure penetration of the electrical field. Basically, the cross-membrane transport of model analytes increased with decreasing electrical resistance of the artificial liquid membrane. However, provided that the artificial liquid membrane and the model analytes were inert to electrode reactions, the following electrode processes occurred in the sample and acceptor solutions, respectively:

Sample Solution: $H_2O \rightarrow 2H^+ + \frac{1}{2}O_2 + 2e^-$

Acceptor solution: $2H^+ + 2e^- \rightarrow H_2$

Basic Analytes

In the sample solution, pH will be adjusted into the acidic range to ensure that the basic model analytes (B) are totally protonated (BH+). Upon application of the electrical potential difference, the protonated model analytes will start their electro-kinetic migration from the sample solution, and in the direction towards the negative electrode placed in the acceptor solution. In the aqueous sample solution, the electrical field strength (V/cm) will be relatively low due to the low electrical resistance of this phase, but nevertheless, because the model analytes are totally protonated, they will rapidly migrate towards the artificial liquid membrane. These rapid migrations will also be promoted by using a thin sample vial which ensures a short migration distance to the artificial membrane. The different model analytes will migrate with different velocity in the sample solution based on their charge to-size ratio, but it is expected only to be a minor factor responsible for the differences observed in their individual transport efficiencies (recovery values).

Secondly, the model analytes will cross the interface to the artificial liquid membrane. In this phase, the electrical field strength (V/cm) will be high due to the high electrical resistance of the organic solvent used. In spite of this, their electrokinetic migration will be strongly suppressed in this medium because deprotonation of the basic substances will (probably) occur in the non-polar medium. In other words, the migration inside the artificial liquid membrane, (is believed) to be strongly controlled by the following equilibrium: $BH^+ \rightarrow B + H^+$ For compounds with a low degree of deprotonation, the electro membrane extraction through the artificial membrane will be relatively high, whereas strongly deprotonating compounds will show a very low electro membrane extraction and will effectively be discriminated by the artificial liquid membrane. This phenomenon is expected to be the principal reason for the differences in the extraction recoveries that will be observed. In addition, differences in the charge-to-size ratios will also be expected to affect the individual transport efficiencies in the artificial liquid membrane.

Extraction of Acidic Drugs

The new device and method of the present invention may be applied to any organic compounds capable of being partly or completely ionized. Thus, for acidic drugs, alkaline conditions in the sample and acceptor solutions are preferred. The sample solution will be made alkaline to pH 12 with NaOH. The porous HFM attached to the vial cap will be dipped in e.g. n-octanol for e.g. 5 seconds to immobilize the solvent in the pores of the HFM. The vial cap with the attached and pretreated HFM will then be placed on top of the sample vial, immersing the HFM into the sample (donor) solution. The sample vial will then be placed in the sample vial compartment and the "lock nut" will be utilized for the second embodiment. A micro syringe preloaded with the acceptor solution will be placed in the syringe holder in both embodiments. In the first embodiment the sample vial compartment will be pushed upwards, guided by the adjustable rail, to immerse the sample electrode (donor phase). In the second embodiment the placement of the syringe in the syringe holder will result in the same. 10 mM NaOH, as acceptor solution will be filled into the lumen of the HFM, immersing the acceptor phase electrode (syringe needle). Both electrodes are steered into their correct positions by the electrode guidance in the vial cap. The vibration unit will be activated and, finally, the electrodes will be connected to a power supply and e.g. 0-300 V will typically be applied for e.g. 5 minutes.

THEORETICAL EXAMPLES

Initial Experiments

The basic experiments will be performed in new devices for electro membrane extraction (EME) as illustrated in FIG. 1-10. The sample (donor) solution, will be filled into a vial and acidified with HCl (PH≈2) prior to EME, to ionize basic analytes of interest or made alkaline with NaOH to ionize acidic analytes of interest. A closed tip polypropylene hollow fiber membrane (HFM) will, by its open end, be attached to the inside funnel of the vial cap, dipped for about 5 s in a organic solvent, serving as the artificial liquid membrane (typically 2-nitrophenyl octyl ether, nitrobenzene, 1-isopropyl nitrobenzene, octanol or heptanol) to immobilize the solvent in the pores of the hollow fiber. This thin layer of organic solvent serve as the artificial liquid membrane, the volume will approximately be 15 µL, with a thickness of approximately 200 µm, corresponding to the wall thickness of the hollow fiber. Excess of solvent will carefully be removed with e.g. a medical wipe. The vial cap with the attached and pretreated HFM will then be placed on top of the sample vial, immersing the HFM into the sample (donor) solution. The sample vial will then be placed in the sample vial holder. In the second embodiment the vial holder will be utilized to connect the vial holder to the rest of the device and securing the vial within the main compartment. A micro syringe preloaded with the acceptor solution will be placed in the syringe holder. In the first embodiment the sample vial compartment will be pushed upwards, guided by the adjustable rail to immerse the sample electrode (donor phase). In the second embodiment the placing of the syringe in the syringe holder after the vial has been placed in the main compartment results in the needle of the syringe being arranged in the lumen of the HFM. In both embodiments approx. 30 µL of a 10 mM hydrochloric acid solution in water will be filled into the lumen of the HFM, immersing the acceptor phase electrode (syringe needle). Both electrodes are steered into their correct positions by the electrode guidance in the vial cap. The vibration unit will be activated and, finally, the electrodes will be connected to a power supply and [e.g. up to] 300 V will typically be applied for [a minimum of] 5 minutes. After electro membrane extraction, the vibration unit will be deactivated/turned off and the acceptor solution will be collected with the micro syringe, and subsequently transferred to a micro insert for further analysis in a dedicated analytical instrument.

One or more out of twenty different basic drugs, will be selected as model analytes to test the new EME devices, namely: Practolol, metaraminol, sotalol, atenolol, cimetidine, hydralazine, nortriptyline, amfetamine, metamfetamine, methadone, hydroxyzine, pethidine, mepyramine, promethazine, haloperidol, fluphenazine, phencyclidine, clomipramine, loperamide and clemastine.

PRACTICAL EXAMPLE

Figure 5:
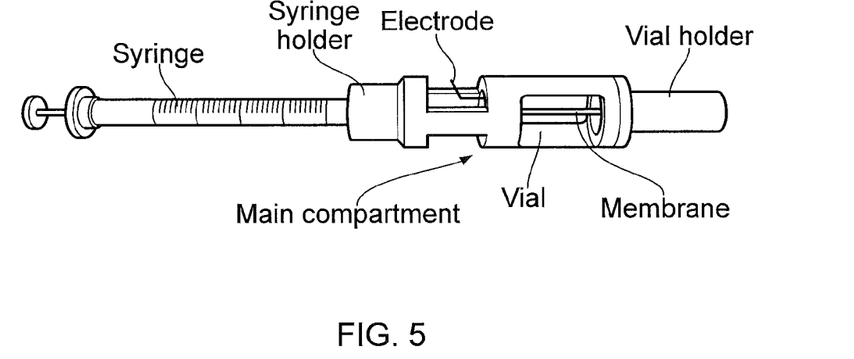
FIG. 5: Illustrates a second embodiment of the electro membrane extraction (EME) unit.
Figure 6:
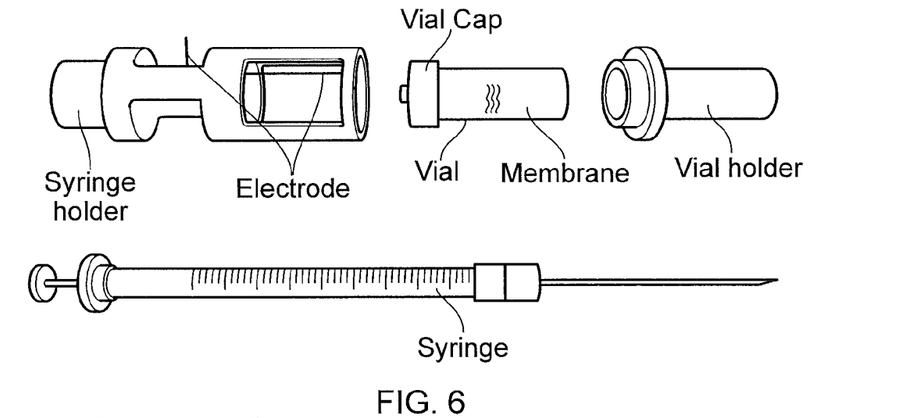
FIG. 6: Shows the different parts of the second embodiment: The main compartment with the single electrode (donor electrode), the vial, the vial cap with the inside funnel for attachment of the membrane, and the syringe with the single electrode (acceptor electrode).
Figure 7:
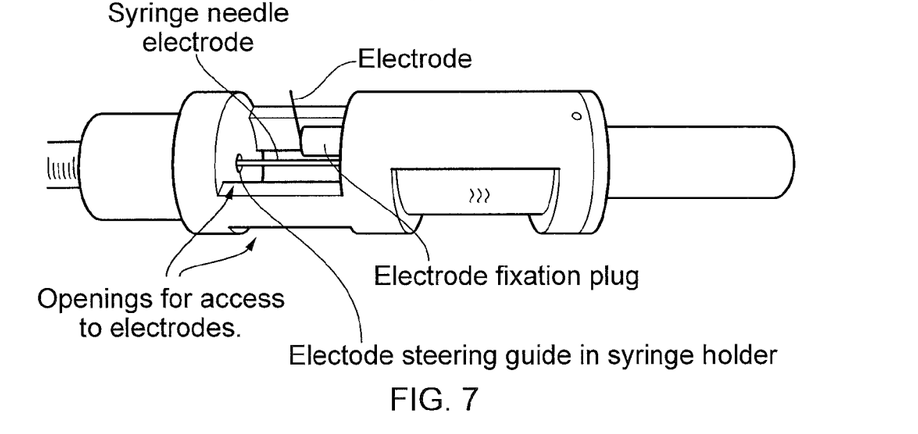
FIG. 7: Shows the detail view of the second embodiment of FIG. 5. The electrodes are accessible for connection through the openings provided between the syringe holder and the main compartment.
Figure 8:
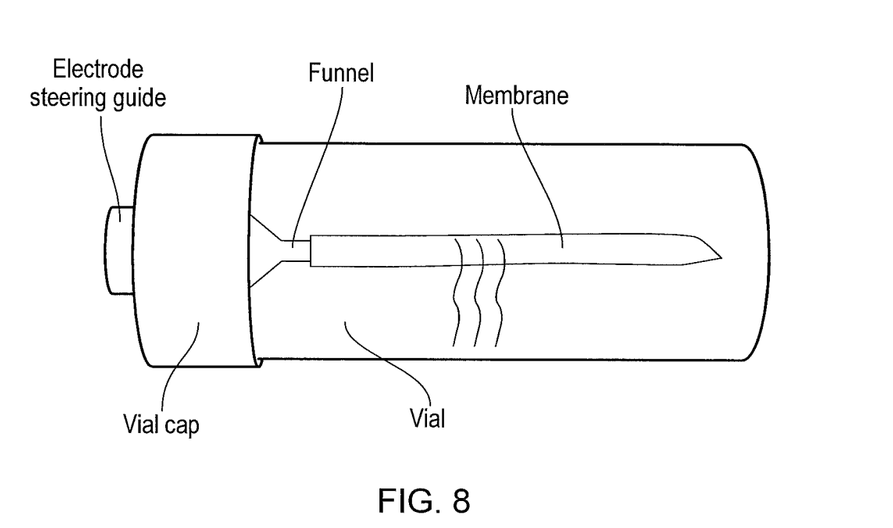
FIG. 8: Shows the vial, and vial cap with the attached membrane.

The main equipment used for the extraction (EME) procedure is shown in FIG. 5, in addition to a power supply with a programmable voltage in the range of 0-300V with a current output in the range of 0-450 mA. The EME device (second embodiment) was agitated on e.g. a Vibramax 100 with an adjustable agitation speed in the range of 0-1500 rpm. The porous hollow fiber used for the SLM (Supported Liquid Membrane) and the housing for the acceptor solution was PP Q3/2 polypropylene hollow fiber membrane from Membrana (Wuppertal, Germany) with an internal diameter of 1.2 mm, a wall thickness of 200 µm and a pore size of 0.2 µm.

Out of the twenty basic drugs, the following five analytes were selected as model analytes for testing of the embodiment according to FIGS. 5-10; pethidine (1), nortriptyline (2), methadone (3), haloperidol (4) and loperamide (5). The sample solution was made up to a total of 1500 µl of the analytes in 10 mM HCl (0.5 µg/ml). EME was performed according to the following procedure; 1500 µl acidified sample (donor phase) solution was filled into the vial. An approx. 23 mm piece of a closed tip polypropylene hollow fiber membrane (HFM), was by its open end attached to the inside funnel of the vial cap, dipped for 5 s in NPOE (2-nitrophenyl octyl ether) serving as the artificial liquid membrane. Excess of NPOE was carefully removed with a medical wipe. The vial cap with the attached and pretreated hollow fiber membrane (SLM) was then placed on top of the sample vial, immersing the SLM into the sample (donor) solution. The sample vial was placed in the sample vial compartment and the vial holder (FIG. 9) was utilized to hold the vial in place. A preloaded micro syringe (acceptor solution) was placed in the syringe holder, and 25 µL of 10 mM acceptor solution was filled into the lumen of the SLM, immersing the acceptor phase electrode (syringe needle). Both electrodes were steered into their correct positions by the electrode guidance in the vial cap and coupled to the power supply. An electrode fixation plug is arranged on around the donor electrode within holder (see FIG. 7). The electrode fixation plug limits the movement of the donor electrode within the vial. The extraction unit was placed on the vibrator. Finally, the vibration unit and power supply was activated at, respectively, 1000 RPM and 200 V for 5 minutes. After the electro membrane extraction, the acceptor solution was collected with the micro syringe, and subsequently transferred to a micro insert for further analysis in a dedicated analytical instrument, e.g. CE (Capillary Electrophoresis)

Several consecutive experiments gave the following average recovery of analyte 1-5;

| | |
|---|---|
| Pethidine (1): | 43% |
| Nortriptyline (2): | 54% |
| Methadone (3): | 68% |
| Haloperidol (4): | 50% |
| Loperamide (5): | 79% |

The invention claimed is:

1. A device for electro membrane extraction (EME), comprising a syringe holder adapted to hold a syringe comprising an acceptor solution; a sample vial holder adapted to hold a sample vial comprising a vial cap, where the vial cap includes an inside funnel to be equipped with a prewetted hollow fiber membrane having a tube like shape sealed at the end distal to the funnel and forming a lumen; the vial cap further comprising steering guides for at least two electrodes; a first electrode to be immersed in a donor solution placed in the sample vial; a second electrode to be immersed, through the funnel in the vial cap, into the lumen of the hollow fiber membrane; and means for sliding the first electrode in and out of the donor solution in the sample vial and for sliding the second electrode in and out of the lumen of the hollow fiber membrane; wherein the device comprises a main compartment arranged to receive the vial, and being releasably closed by connection of the vial holder or the vial cap thereto.

2. Device according to claim 1, wherein the device further comprises a vibration/agitation unit.

3. Device according to claim 1, wherein the syringe comprises a needle and the needle is used as the second electrode.

4. Device according to claim 1, wherein the vial cap comprises a centrally arranged guide for the second electrode and a decentralized guide for the first electrode.

5. A method for electro membrane extraction (EME) of an organic compound in a 3-phase system using a device comprising:
a syringe holder adapted to hold a syringe comprising an acceptor solution;
a sample vial holder adapted to hold a sample vial comprising a vial cap, where the vial cap includes an inside funnel to be equipped with a prewetted hollow fiber membrane (HFM) having a tube like shape sealed at the end distal to the funnel and forming a lumen; the vial cap further comprising steering guides for at least two electrodes;
a first electrode to be immersed in a donor solution placed in the sample vial;
a second electrode to be immersed, through the funnel in the vial cap, into the lumen of the hollow fiber membrane;
means for sliding the first electrode in and out of the donor solution in the sample vial and for sliding the second electrode in and out of the lumen of the hollow fiber membrane; and
a main compartment arranged to receive the vial, and being releasably closed by connection of the vial holder or the vial cap thereto, the method comprising the steps of:
providing, as the donor solution, a sample solution comprising at least one organic compound to be extracted in the sample vial,
attaching the HFM hollow fiber membrane (HFM) to the funnel arranged on the inside of the cap,
dipping the HFM in an organic solvent, thereby forming an artificial liquid membrane;
placing the vial cap on top of the sample vial, immersing the HFM into the sample solution;
placing a sample electrode, as the first electrode, in the sample solution;
placing a needle of a micro syringe, as the second electrode, within the inner lumen of the HFM, where the micro syringe comprises the acceptor solution;
injecting the acceptor solution into the inner lumen of the HFM;
applying power over the sample electrode and the needle to promote the migration of said organic compound from the sample solution through the liquid membrane to the acceptor solution.

6. Process according to claim 5, further comprising switching off the power supply and retracting the acceptor solution into the micro syringe.

7. Process according to claim 5, further comprising agitating the sample by vibration.

8. Process according to claim 5, where the needle is placed within the lumen of the HFM and the electrode is placed within the sample solution in one step.

9. Process according to claim 6, where the acceptor solution is transferred to a micro insert for further analysis in a dedicated analytical instrument.

* * * * *